(12) United States Patent
Liu et al.

(10) Patent No.: US 6,825,928 B2
(45) Date of Patent: Nov. 30, 2004

(54) DEPTH-RESOLVED FLUORESCENCE INSTRUMENT

(75) Inventors: Quan Liu, Madison, WI (US); Nirmala Ramanujam, Madison, WI (US); Changfang Zhu, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/322,907

(22) Filed: Dec. 18, 2002

(65) Prior Publication Data

US 2003/0220549 A1 Nov. 27, 2003

Related U.S. Application Data

(60) Provisional application No. 60/341,971, filed on Dec. 19, 2001, and provisional application No. 60/370,134, filed on Apr. 5, 2002.

(51) Int. Cl.[7] ............................. G01N 21/64; A61B 5/00

(52) U.S. Cl. ........................ 356/317; 250/458.1; 600/317

(58) Field of Search ................................ 356/317, 318, 356/417; 250/458.1, 459.1, 461.1, 461.2; 600/317

(56) References Cited

U.S. PATENT DOCUMENTS

6,014,204 A * 1/2000 Prahl et al. .................... 356/73

* cited by examiner

*Primary Examiner*—F. L. Evans
(74) *Attorney, Agent, or Firm*—Quarles & Brady LLP

(57) ABSTRACT

A fluorescence instrument illuminates the surface of tissue with light of a selected wavelength and light emanating from the tissue due to fluorescence is collected. The size of the effective illumination/collection aperture is varied to probe at various depths beneath the surface of the tissue for a fluorescence layer. Three embodiments of the instrument are described.

11 Claims, 8 Drawing Sheets

DEPTH-RESOLVED FLUORESCENCE INSTRUMENT

CROSS-REFERENCE TO RELATED APPLICATIONS

This application claims the benefit of U.S. Provisional Application No. 60/341,971, filed on Dec. 19, 2001 and entitled "Quantitative Fluorescence Imaging", and U.S. Provisional Application No. 60/370,134, filed on Apr. 5, 2002 and entitled "Novel Probe Design For Measuring Depth Dependent Fluorescence From Epithelial Tissues".

STATEMENT REGARDING FEDERALLY SPONSORED RESEARCH

This invention was made with government support under Grant No. CA82710 awarded by the National Institute of Health. The United States Government has certain rights in this invention.

BACKGROUND OF THE INVENTION

The field of the invention is fluorescence spectroscopy and imaging, and in particular, the use of fluorescence to detect epithelial pre-cancers and cancers.

Fluorescence spectroscopy and imaging in the ultraviolet-visible (UV-VIS) wavelength spectrum is an exciting new modality for detecting human epithelial pre-cancer and cancer. Fluorescence spectroscopy is performed by irradiating the tissue surface with light and detecting the fluorescent light emitted by "fluorophores" in the tissue. The fluorophores may be "endogenous" molecules that absorb the impinging photons and emit photons at a different wavelength, or they may be "exogenous" fluorophores such as injected photosensitizing agents. This emerging technology has shown promising results for detecting early neoplastic growth in a variety of organ sites including the colon, bronchus, cervix, oral cavity, skin and bladder. Noninvasive and fast detection of epithelial pre-cancers and early cancers through the use of fluorescence spectroscopy can significantly improve the efficacy and reduce cost of cancer screening and diagnostic programs.

One of the most widely explored applications of fluorescence spectroscopy is the detection of endoscopically invisible, early neoplastic growth in epithelial tissue sites. Early neoplastic growth refers to pre-malignant changes such as dysplasia and carcinoma in situ (CIS), which precede malignancy, i.e., invasive carcinoma. Currently, there are no effective and commonly accepted diagnostic techniques for these early tissue transformations. Fluorescence spectroscopy is ideally suited for this application because of its ability to examine tissue surfaces, rather than tissue volumes, and the ability to deploy this technology in an endoscopic device. If fluorescence spectroscopy can be applied successfully as a diagnostic technique in this clinical context, it may increase the potential for curative treatment, and thus, reduce complications. In addition to the potential for improved patient outcome, the fast and noninvasive nature of this diagnostic technique may also reduce health care costs.

Referring to FIG. 1, when a biologic molecule is illuminated at an excitation wavelength, which lies within the absorption spectrum of that molecule, it will absorb photons' energy and be activated from its ground state (state of lowest energy; $S_0$) to an excited state (state of higher energy; $S_1$). The molecule can then relax back from the excited state to the ground state by generating energy in the form of fluorescence, at emission wavelengths, which are longer than the excitation wavelength. The phenomenon of fluorescence displays several general characteristics for a particular biologic molecule. First, due to losses in energy between absorption and emission, fluorescence occurs at emission wavelengths, which are always red-shifted, relative to the excitation wavelength. Second, the emission wavelengths of fluorescence are independent of the excitation wavelength. Third, the fluorescence spectrum of a biologic molecule is generally a mirror image of its absorption spectrum. The fluorescence of a biologic molecule is characterized by its quantum yield and its lifetime. The quantum yield is simply the ratio of the energy converted to fluorescence to the energy absorbed. The lifetime is defined as the average time the biologic molecule spends in the excited state before returning to the ground state. The fluorescence quantum yield and lifetime are modified by a number of factors that can increase or decrease the energy losses. For example, a molecule may be non-fluorescent as a result of a large rate of non-radiative decay (thermal generation).

Fluorescence spectroscopy is the measurement and analysis of various features that are related to the fluorescence quantum yield and/or lifetime of a biologic molecule (s). The fluorescence intensity of a biologic molecule is a function of its concentration, its extinction coefficient (absorbing power) at the excitation wavelength, and its quantum yield at the emission wavelength. A fluorescence emission spectrum represents the fluorescence intensity measured over a range of emission wavelengths, at a fixed excitation wavelength. Conversely, a fluorescence excitation spectrum is a plot of the fluorescence intensity at a particular emission wavelength, for a range of excitation wavelengths. A fluorescence, excitation-emission matrix (EEM) is a two dimensional contour plot, which displays the fluorescence intensities as a function of a range of excitation and emission wavelengths. Each contour represents points of equal fluorescence intensity. Finally, fluorescence lifetime measurements are represented as the fluorescence intensity distributed over a very short time scale, at a fixed excitation-emission wavelength pair. FIGS. 2a–2d are graphic illustrations of a fluorescence (a) emission spectrum, (b) excitation spectrum, (c) EEM and (d) decay profile.

Table 1 shows a list of biologic endogenous fluorophores and their excitation and emission maxima. These endogenous fluorophores include the amino acids, structural proteins, enzymes and coenzymes, vitamins, lipids and porphyrins. Their excitation maxima range lies between 250 and 450 nm (which spans the ultraviolet and visible spectral range), whereas their emission maxima range lies between 280 and 700 nm (which spans the ultraviolet, visible and near-infrared spectral range). Fluorophores that are believed to play a role in transformations that occur in the neoplastic process in tissue, are the amino acids, tryptophan, the structural protein, collagen, the co-enzymes, NADH and FAD and porphyrins.

TABLE 1

| Endogenous Fluorophores | Excitation Maxima (nm) | Emission Maxima (nm) |
|---|---|---|
| Amino acids | | |
| Tryptophan | 280 | 350 |
| Tyrosine | 275 | 300 |
| Phenylalanine | 260 | 280 |

TABLE 1-continued

| Endogenous Fluorophores | Excitation Maxima (nm) | Emission Maxima (nm) |
|---|---|---|
| Structural Proteins | | |
| Collagen | 325, 360 | 400, 405 |
| Elastin | 290, 325 | 340, 400 |
| Enzymes and Coenzymes | | |
| FAD, Flavins | 450 | 535 |
| NADH | 290, 351 | 440, 460 |
| NADPH | 336 | 464 |
| [NADH, reduced nicotinamide dinucelotide; NAD(P)H, reduced nicotinamide dinucleotide phosphate; FAD, flavin adenine dinucleotide.] | | |
| Vitamins | | |
| Vitamins A | 327 | 510 |
| Vitamins K | 335 | 480 |
| Vitamins D | 390 | 480 |
| Vitamins $B_6$ compounds | | |
| Pyridoxine | 332, 340 | 400 |
| Pyridoxamine | 335 | 400 |
| Pyridoxal | 330 | 385 |
| Pyridoxic acid | 315 | 425 |
| Pyridoxal phosphate | 5'-330 | 400 |
| Vitamin $B_{12}$ | 275 | 305 |
| Lipids | | |
| Phospholipids | 436 | 540, 560 |
| Lipofuscin | 340–395 | 540, 430–460 |
| Ceroid | 340–395 | 430–460, 540 |
| Porphyrins | 400–450 | 630, 690 |

Fluorescence spectroscopy of turbid media such as tissue depends on any of a number of factors. It depends on the concentration and distribution of fluorophore(s) present in the tissue, as well as the biochemical/biophysical environment, which may alter the quantum yield and lifetime of the fluorophore(s). For example, epithelial tissues, generally have two primary sub-layers: a surface epithelium and an underlying stroma or submucosa; the specific fluorophores, as well as their concentration and distribution can vary significantly in these two tissue layers with a neoplastic change. Fluorescence spectroscopy of turbid media such as tissue also depends on the absorption and scattering that results from the concentration and distribution of nonfluorescent absorbers and scatterers, respectively, within the different sub-layers of the tissue.

The effect of the aforementioned factors on fluorescence spectroscopy of tissue is wavelength-dependent. First, the fluorophores that have absorption bands that lie in the same wavelength range as the excitation light will be excited and hence, emit fluorescence. The absorption and scattering properties of the tissue will affect light at both excitation and emission wavelengths. Therefore, only those fluorophores contained in the tissue layers to which the excitation light penetrates and from which, the emitted light can escape the tissue surface will produce measurable fluorescence. Elastic scattering events in tissue are caused by random spatial variations in the density, refractive index, and dielectric constants of extracellular, cellular and subcellular components. Tissue scattering generally decreases monotonically with increasing wavelength over the ultraviolet (UV), visible (VIS) and near-infrared (NIR) spectral regions.

Although absorption in tissue is strongly wavelength-dependent, it tends to generally decrease with increasing wavelengths. Consequently, the penetration depth of light, which is primarily a function of the tissue absorption properties, decreases from several centimeters to a few hundred microns, from the near infrared to the ultraviolet. For example, in the UV spectral region, the penetration depth of light in tissue is approximately 225 $\mu$m at 337 nm.

The illumination and collection geometry of the excitation and the emitted light, respectively, can also affect the fluorescence measurement from tissue, with respect to both the intensity and line shape. This may be attributed to the fact that although the fluorescence is generated approximately isotropically from the fluorophores within a medium, the fluorescence emitted from its surface may range from isotropic to anisotropic depending on whether the medium is highly absorbing, dilute or turbid. Monte Carlo simulations have been used extensively to simulate light distribution in turbid media to explore the effect of absorption and scattering on the fluorescence emitted from the surface, using finite excitation beam profiles and complex excitation and emission geometries.

Fluorescence measurements have been performed on biologic fluids, single cells, cell suspensions, frozen tissue sections and from bulk tissues, both in vitro and in vivo. The various types of instruments employed for these measurements, essentially have the same basic components. A schematic of the basic components of such an, instrument is shown in FIG. 3. It consists of a monochromatic excitation light source, a flexible, delivery and collection conduit for the delivery of excitation light to and the collection of the emitted light from the biologic medium, a dispersing element, which separates the emitted light into its respective wavelengths and a detector, which measures the intensity at the emission wavelength (s).

Generally, monochromatic excitation light sources are used and include ultraviolet and visible arc lamps (mercury, xenon) followed by a bandpass filter and continuous wave (Argon ion-ultraviolet lines, Helium-Cadmium—442 nm) or pulsed lasers (nitrogen—337 nm; the addition of dyes in an attached resonant cavity provides additional visible wavelengths). Lasers have the advantage of efficient coupling into fiber-optic probes. However, filtered arc lamps have the advantage of excitation wavelength tunability, when used with a series of band pass filters or a monochromator and they are generally, more portable. It should be noted that pulsed lasers, with very short pulse durations (in the order of nanoseconds) are necessary when the biologic medium needs to be illuminated with pulsed excitation light for gated detection (which provides effective rejection of ambient light during florescence measurements) and for fluorescence lifetime measurements.

Two approaches are used to illuminate and collect light from tissues. The first approach is to use fiber-optic probes that are placed directly in contact with the tissue (contact approach), and the second approach is to use a series of lenses to project the light onto the surface and collect it, in a similar manner (non-contact approach). With the contact approach, variable pressure on the biologic medium may distort the fluorescence spectrum. However, with the non-contact approach, the fluorescence intensity will vary with the variable, source-sample and sample-detector distance. In general, the contact approach is used for steady-state and time-resolved, fluorescence measurements from small tissue areas, whereas the non-contact approach is more suited for fluorescence imaging from relatively larger areas of tissue.

Light can be spectrally dispersed using a monochromator or a spectrograph, which are both dispersing components. A monochromator presents one wavelength or band pass at a time of the input light from its exit slit, whereas a spectrograph presents a range of wavelengths of the input light, simultaneously at the exit focal plane. Monochromators can be used as filters in conjunction with arc lamps to produce monochromatic excitation light at a series of wavelengths (if only several excitation wavelengths are needed, band pass filters are more appropriate). Monochromators can also be used to disperse the emitted light into its respective wavelengths, each of which can be detected serially using a single-channel detector. However, spectrographs can be used to disperse the emitted light into its respective wavelengths, simultaneously, for multi-channel detection.

The important considerations in choosing a detector are the type of measurements being made, i.e., single wavelength versus multi-wavelength and single-pixel (small area measurements) versus multi-pixel (large area measurements). Fluorescence measurements from single-pixels can be made either using a single-channel or multi-channel detector. If fluorescence intensity at only one or several wavelengths is being measured, single-channel, photo emissive tubes called photo multiplier tubes (PMT) or semi-conductor based, avalanche photodiodes (APD), with band pass filters can be used. For fluorescence spectroscopy, a spectrograph coupled to a multi-channel, photo diode array is appropriate. Fluorescence spectroscopy can also be performed using a monochromator coupled to a PMT. In the case of fluorescence imaging from multiple pixels, a two-dimensional, charged coupled device (CCD) camera, with band pass filters may be employed. To reduce or eliminate the detection of ambient light, a detector with an intensifier for fast gating (several nanoseconds) is used in conjunction with a pulsed excitation light source. Also, in order to minimize the detection of the back-scattered excitation light, which is much stronger than the weaker emitted light, optical components, such as long pass or dichroic filters may be employed in front of the detection system.

Single-pixel (<2 mm, diameter of tissue area) measurements of tissue fluorescence spectra, in vivo have been performed mostly using a pulsed excitation light source, a fiber-optic probe (contact approach), a spectrograph and an intensified photo diode array. The transient fluorescence decay profiles at a specific excitation-emission wavelength pair have also been measured using a similar instrument, except that the spectrograph and multi-channel, photo diode array have been replaced by a filtered, single-channel PMT or APD. Finally, fluorescence imaging from multiple pixels of tissue, in vivo (tissue area is a few centimeters in diameter) has been performed with a non-contact approach using a continuous wave laser in combination with a band pass filter and a CCD camera. Measurements with single-pixel and multi-pixel instruments generally require several seconds to a minute in a clinical setting.

Fluorescence spectroscopy in the ultraviolet and visible spectral regions has been developed and employed to differentiate diseased from non-diseased tissues, in vivo. The altered biochemical and morphologic state that occurs as tissue progresses from a non-diseased to diseased state, is reflected in the spectral characteristics of the measured fluorescence. This spectral information can be compared to tissue histology, the current gold standard, which indicates the absence or presence and grade of disease. Mathematical algorithms can then be developed and used to classify tissues into their respective histologic category, based on their spectral features. These mathematical algorithms can be implemented in software, thereby enabling fast, non-invasive, automated screening and diagnosis in a clinical setting.

There are generally two steps involved in the development of a mathematical algorithm, which is based on fluorescence spectroscopy. The first step is to dimensionally reduce the measured spectral variables. The second step is to develop a classification scheme for the discrimination of these useful spectral parameters into relevant histologic/histo-pathological categories. The development of current mathematical algorithms based on fluorescence spectroscopy can be classified broadly into three categories: 1) algorithms based on qualitatively selected spectral variables (fluorescence intensities at several emission wavelengths), 2) algorithms based on statistically selected spectral parameters (a more robust evaluation and use of all the measured spectral information) and 3) algorithms based on parameters that reflect the biochemical and/or morphologic features of the tissue. Classification schemes employ either a binary or probability based discrimination. In most cases, algorithms are based on qualitatively or statistically selected spectral variables in conjunction with binary classification methods.

While current fluorescence spectroscopy and imaging methods detect neoplastic tissue areas, their sensitivity to the neoplastic layer in tissue is limited by how much of the probing volume intercepts the target of interest. In other words, the probing depth is fixed by the illumination and collection geometry. However, the depth and thickness of the neoplastic growth can vary and the sensing volume may not be optimized for maximal contrast. Being able to maximize the contrast between the neoplastic growth and normal tissue will significantly enhance the diagnostic capability of this technology.

SUMMARY OF THE INVENTION

The present invention employs a fluorescence instrument and method to characterize the depth dependent distribution of a fluorescent target (e.g., pre-cancer or cancer) in a turbid medium (e.g., epithelial tissue). More specifically, a fluorescence strategy is employed in which each discrete site is examined with variable size, illumination and collection apertures to measure the depth dependent distribution of the fluorescence target.

A general object of the invention is to maximize the fluorescence contrast from pre-cancerous and early cancerous growth in human epithelial tissues through the detection of endogenous fluorophores and contrast agents. Providing insight into the depth dependent distribution of pre-cancers and early cancers in human epithelial tissues is important in maximizing the differences in the endogenous fluorescence between epithelial pre-cancers and cancers and non-neoplastic tissue.

Another object is to provide a fluorescence instrument which enables the measurement of fluorescent targets at various depths below the surface of a turbid medium such as tissue. This depth-profiling fluorescence method is adaptable to current endoscopic optical imaging systems without significantly increasing their complexity or cost.

The foregoing and other objects and advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

GENERAL DESCRIPTION OF THE INVENTION

The feasibility of probing the depth and thickness of a fluorescent target in a turbid medium via fluorescence detection using variable diameter, illumination and collection apertures on the sample surface that have a coincident optical path will now be described. First, a theoretical model of a biologically relevant system is established. Next, a Monte Carlo code was developed to simulate fluorescent light propagation through this medium. Then, simulations were performed for a range of coincident, illumination-collection aperture-diameters on the surface of the medium.

Figure 1:
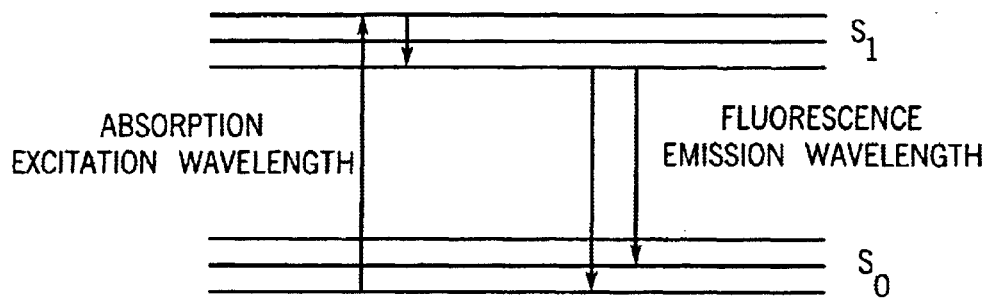
FIG. 1 is an energy level diagram illustrating the phenomena of absorption and fluorescence.
Figure 2A:
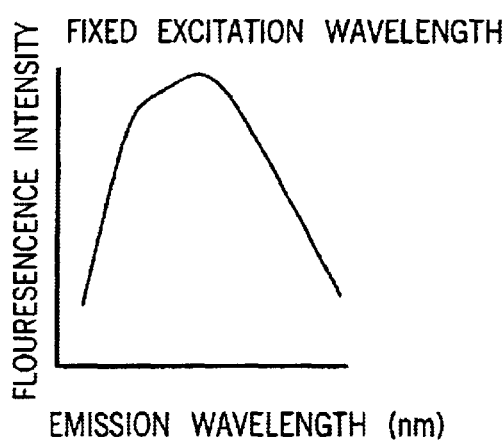
FIGS. 2a–2d are graphic representations of different fluorescence characteristics.
Figure 2B:
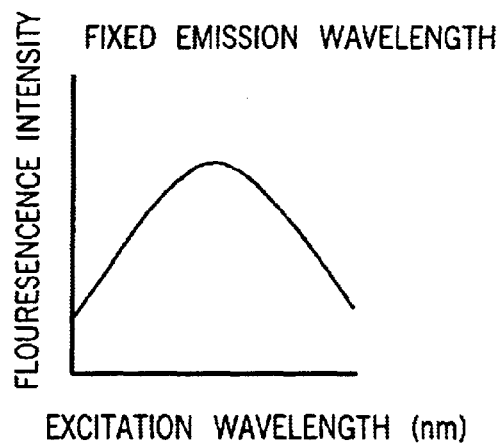
Figure 2C:
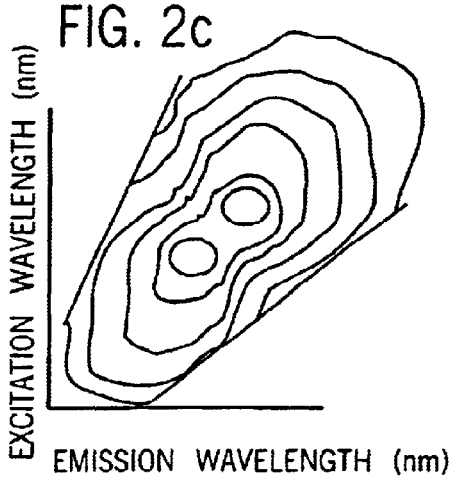
Figure 2D:
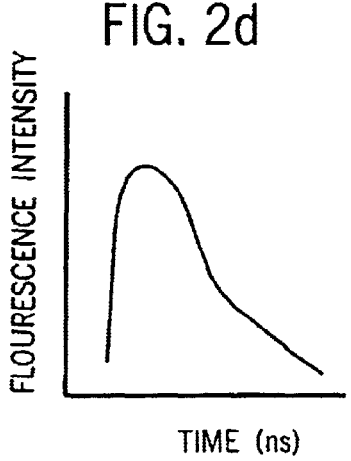
Figure 3:
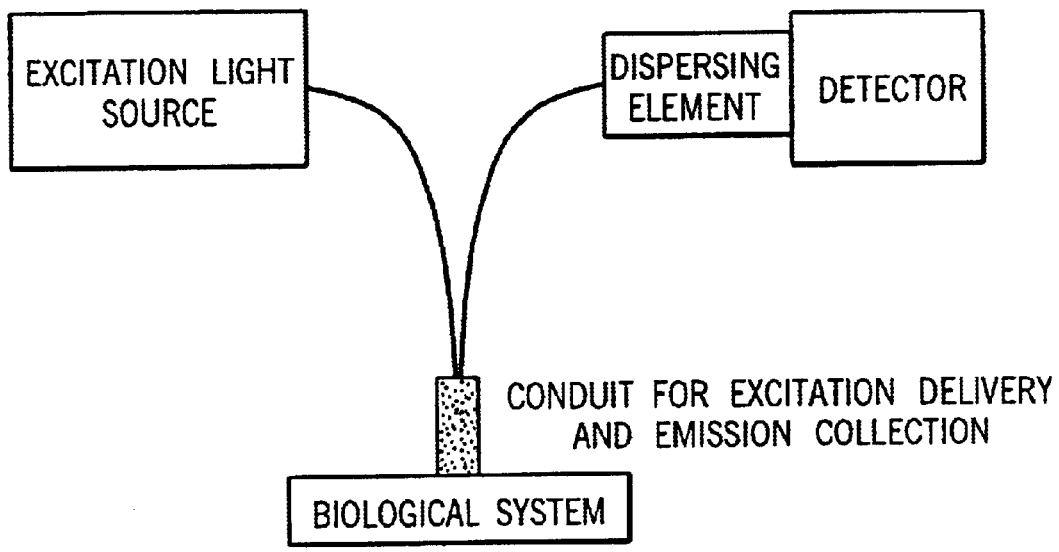
FIG. 3 is a block diagram of a conventional fluorescence spectroscopy instrument.
Figure 4:
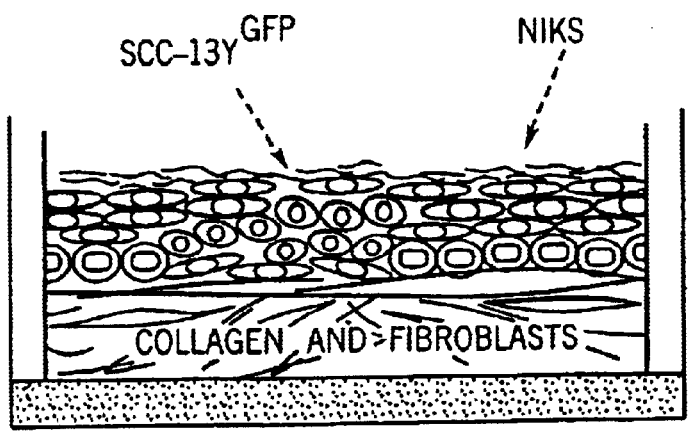
FIG. 4 is an illustration of a tissue culture model of squamous cell carcinoma.

The biological model: A tissue culture model of squamous cell carcinoma (SCC) is shown in FIG. 4. The tissue culture has two layers; a superficial epithelium that is several cell layers thick and which, consists of normal immortalized keratinocytes (NIKs), and an underlying extracellular matrix, which consists of collagen and fibroblasts. The SCCs are inserted into the basal membrane of the epithelium and these cells proliferate over time. It has been shown that the SCC proliferation progresses upward within the epithelium before these cells progress downward and invade the basement membrane. The SCCs can be transfected with the molecular reporter, green fluorescent protein (GFP). Although the SCC tissue culture model has no vasculature, its structure and biological properties mimic that of intact epithelial neoplasia very well.

Figure 5:
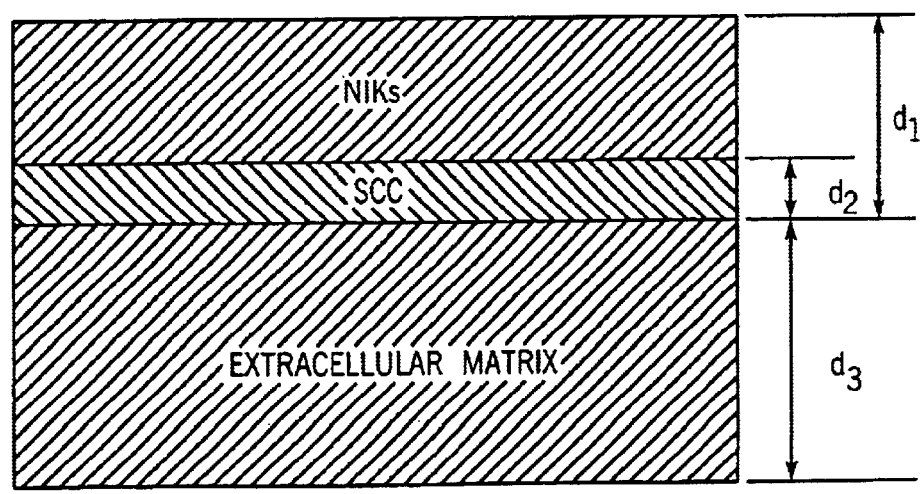
FIG. 5 is a schematic representation of a tissue culture model.

The theoretical model: A theoretical model that closely approximates the tissue culture system is shown in FIG. 5. The model has two primary layers; a normal epithelium layer, which consists of NIKs and an underlying extracellular matrix layer. To simulate the proliferation of SCCs, an additional layer is introduced in the base of the epithelium, the thickness of which ranges from zero to the full thickness of the epithelium, to signify the extent of proliferation. The following parameters are identified for the theoretical model: (1) the dimensions and (2) the optical properties and fluorescence efficiency of each layer, at a particular excitation and emission wavelength. High-resolution fluorescence imaging was used to characterize the auto fluorescence distributions in cross-sections of freeze-trapped neoplastic and non-neoplastic human cervical tissues at the excitation-emission wavelength pairs: 365, 460 nm and 460, 520 nm. The results of this study were used to define the parameters of the theoretical model.

Table 2 summarizes the parameters of the model. The thickness of the NIKs and extracellular matrix layer was defined from the results of cervical tissue studies. The thickness of the SCC layer was assumed to be, variable with maximal thickness equivalent to that of the epithelium, while the total thickness of the epithelium layer and SCC layer were fixed. Therefore, both the depth and the thickness of the SCC layer were varied simultaneously. The lateral dimension of the model is assumed to be, infinitely wide. The auto fluorescence properties of the cervical tissues at the excitation emission wavelength pair, 460, 520 nm were used to assign the fluorescence efficiency values of the NIKs, SCC and extracellular matrix layers. Fluorescence characterization of GFP tagged SCCs (abbr. SCC-GFP) in suspension was performed. The SCC-GFP fluorescence efficiency was maximal near the excitation-emission wavelength pair, 460, 520 nm and was a factor of fourteen higher than the auto fluorescence of SCCs in suspension. The absorption coefficient ($\mu_a$), reduced scattering coefficient ($\mu_s'$) and the anisotropy factor (g) at 460 and 520 nm were obtained from the literature. As a first approximation, these values were assumed to be, identical for all three layers of the model. The refractive index of the model was set at 1.37.

TABLE 2

Parameters of the model (NIKs-normal immortalized keratinocytes, SCC-squamous cell carcinoma, SCCGFP-green fluorescent protein (GFP) transfected SCCs, $\mu_a$-absorption coefficient, $\mu_s'$-reduced scattering coefficient, g-anisotropy, $\lambda_{exc}$-excitation wavelength and $\lambda_{emm}$-emission wavelength).

| Layer | Thickness (μm) | Fluorescence Efficiency at $\lambda_{exc}$, $\lambda_{emm}$:460, 520 nm | $\mu_a$, $\mu_s'$, (1/cm) and g at $\lambda_{exc:460\ nm}$ | $\mu_a$, $\mu_s'$, (1/cm) and g at $\lambda_{exc:520\ nm}$ |
|---|---|---|---|---|
| NIKs | 450 | 0.2 | 12, 7.2, 0.94 | 8.3, 7.52, 0.94 |
| SCC | 0–450 | 0.05 | 12, 7.2, 0.94 | 8.3, 7.52, 0.94 |
| SCCGFP | | 0.7 | | |
| Extracellular Matrix | 2000 | 0.6 | 12, 7.2, 0.94 | 8.3, 7.52, 0.94 |

Computational modeling of fluorescent light propagation in the model was carried out using software that was modified from a three-dimensional, weighted-photon Monte Carlo code. The Monte Carlo method simulates the random walk of "discrete photons" in a turbid medium that contains absorbers and scatterers. The two key decisions are: (1) the mean free path for a scattering and absorption event, and (2) the direction in which the photon moves after a scattering event. At a boundary, the photon is either reflected or moves across the interface. The number of photons required depends on the precision needed.

Photons were launched at random, uniformly distributed locations across the model surface over a range of angles within that defined by a numerical aperture of 0.37 and over a specific illumination area. A rejection scheme was used to determine whether an absorbed fraction of the photon packet within the medium is dissipated as heat or re-emitted as a fluorescent photon. The fluorescence that escapes the medium was collected over an area and numerical aperture that was identical to that defined for the illumination. Furthermore, the illumination and collection areas were coincident on the sample surface and varied simultaneously from 10–800 $\mu$m. A total of 10,000,000 photons were launched in each simulation (computational time was approximately 7 hours per simulation).

Figure 6A:
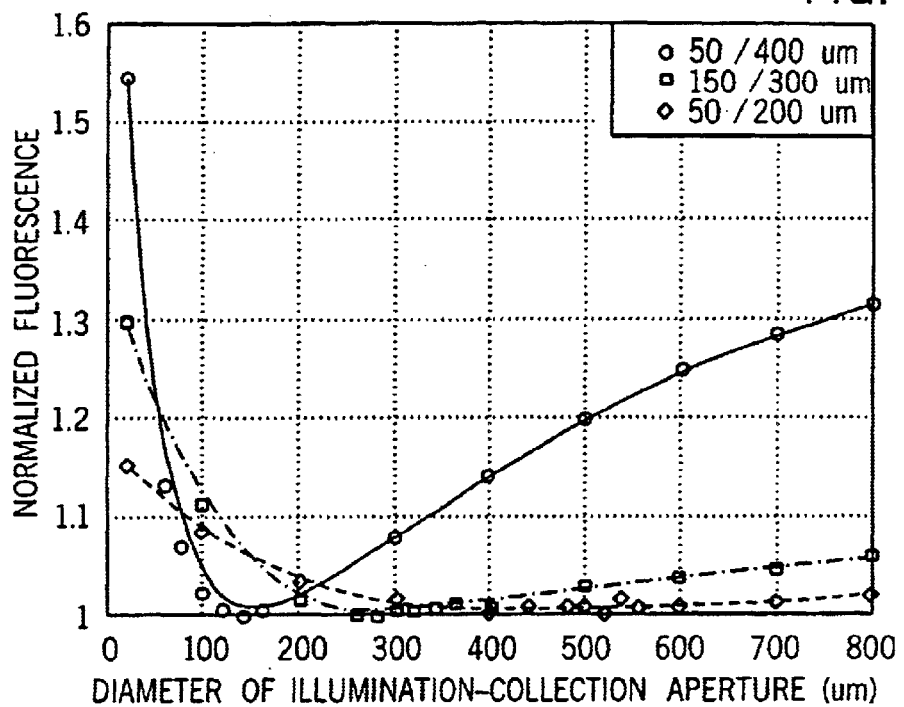
FIGS. 6a–6b are graphic representations of normalized fluorescence measurements versus illumination/collection aperture for the tissue model of FIG. 5 in the absence and presence of an exogenous fluorophore (GFP), based on Monte Carlo simulation results.
Figure 6B:
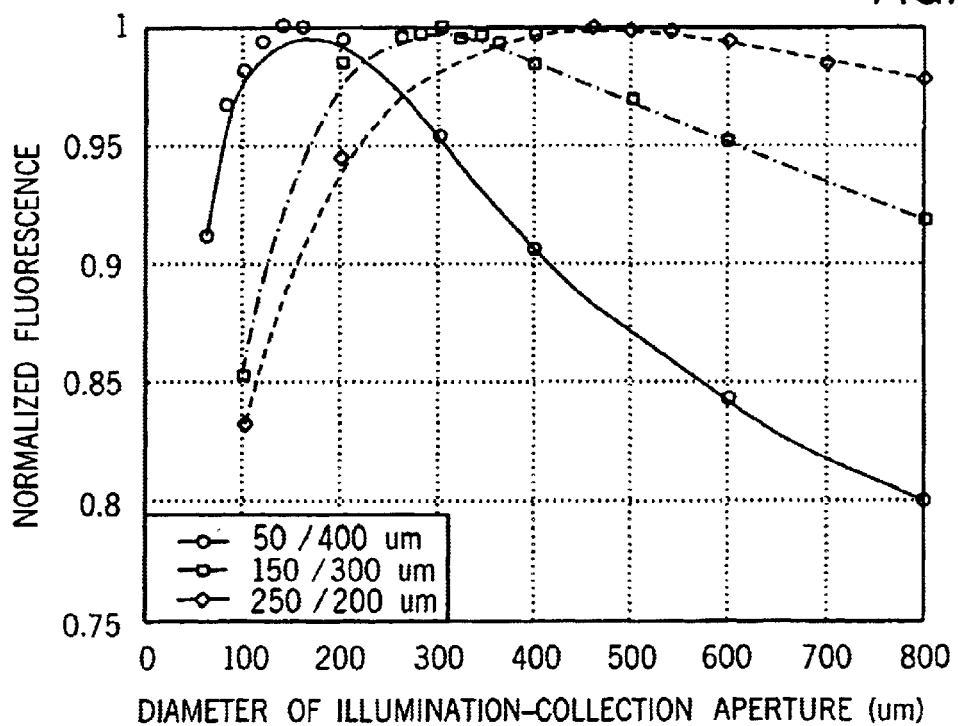

FIGS. 6a and 6b show the resulting fluorescence response versus diameter of the illumination-collection aperture for the model in FIG. 5. Results are shown for: (a) the SCC layer without GFP and (b) the SCC layer with GFP (SCCGFP). Each curve represents the ratio of two profiles; the fluorescence detected for a model containing a finite SCC layer thickness and that detected for a model containing a "zero $\mu$m" thickness SCC layer (equivalent to a normal epithelium). The normalized plots have been autoscaled to facilitate comparison of the profiles obtained for different SCC depths/thicknesses. The results in FIG. 6 shows that each normalized fluorescence profile has a minimum (auto fluorescence) or a maximum (GFP fluorescence). The aperture diameter corresponding to this minimum/maximum shifts to larger values with increasing depth (and decreasing thickness) of the SCC layer. However, as the SCC layer depth increases, the uncertainty in the aperture diameter that corresponds to the minimum/maximum also increases.

Figure 7:
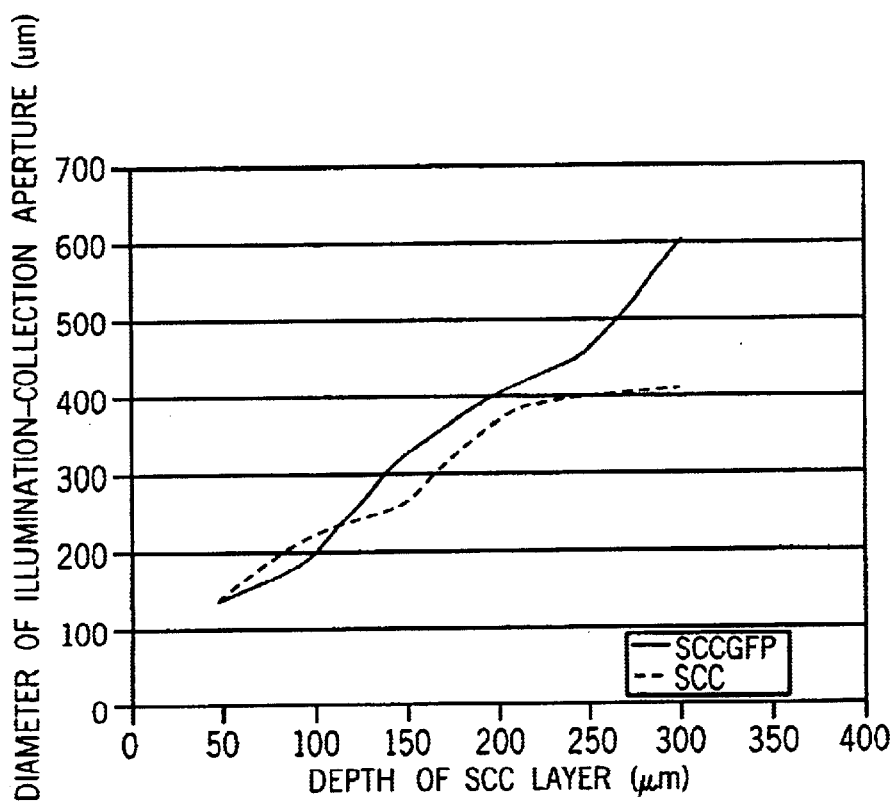
FIG. 7 is a graphic representation showing the relationship of illumination/collection aperture versus depth of the SCC tissue layer in the model of FIG. 5.

FIG. 7 is a plot of the diameter of the illumination-collection aperture that corresponds to the minimum (in SCC case) and maximum (in SCCGFP case) normalized fluorescence versus the depth of the SCC layer. There is a linear relationship between aperture diameter and depth. The slope of the fitted line is independent of the fluorescence efficiency, except at the sensitivity limit for SCC auto fluorescence. An inverse relationship is observed between aperture size and the SCC layer thickness (not shown). The depth from which 80% of the detected fluorescence originates for the aperture diameter range shown in FIG. 6 was 200–750 $\mu$m.

This technique can be used not only in the detection of pre-cancers in tissues but also in locating an optical heterogeneity in a turbid medium. In our case, fluorescence is measured because fluorescence carries information selectively about certain substances in tissues related to neoplastic changes. Other quantities can be employed as long as they carry information of interest and they are discernibly different between the target and surrounding medium.

The discovery of this relationship between fluorescence illumination/collection aperture and the depth of the SCC layer is the basis for instruments that maximize the fluorescence contrast from pre-cancers and cancers in epithelial tissues. In one embodiment described in detail below a single optical fiber bundle is employed to both illuminate the surface of the target and collect light emanating from the same surface. The effective aperture size of this single optical fiber bundle is varied to carry out the present invention. In this embodiment the illumination and collection apertures overlap.

Another discovery is that the depth of a fluorescence layer may be probed with an instrument in which the illumination and collection apertures do not overlap. In this alternative instrument, illumination is provided through one fiber that rests against the tissue surface at one location and light is collected by a separate fiber that rests against the tissue at a different location. The diameter of the illumination fiber and the diameter of the collection fiber remains fixed. The variation in the "effective" illumination/collection aperture size, however, is achieved by changing the center-to-center distance between the illumination and collection fibers. Aperture size is varied by moving the single collection fiber to different locations, or by providing separate, fixed collection fibers at each location. In order to enable the same shallow probing depth as the "overlap" instrument, the illumination source on this non-overlap instrument is tilted by 45 degrees so that the detected fluorescence is sensitive to the same tissue depths as those described above. The following Table 3 compares the percent fluorescence detected and the 80% probing depth achieved respectively with the overlapping collection approach described above and the non-overlapping, multiple fiber approach. The data was obtained by simulation on the same tissue model shown in FIG. 5. Note that in these simulations, $d_2$ is set to zero.

TABLE 3

|  | 80% Probing Depth ($\mu$m) | Fluorescence Detected |
|---|---|---|
| Overlapping Collection: Varying Aperture (200–1000 $\mu$m) | 470~760 | $7.5 \times 10^{-4}$~$2.4 \times 10^{-3}$ |
| Non-Overlapping Collection: Varying distance (200–1000 $\mu$m) | 275~815 | $8.4 \times 10^{-4}$~$4.1 \times 10^{-3}$ |

As shown in the Table 3, ranges for the two approaches are similar, which suggests that both of them can be used in the detection of pre-cancers in tissues. The non-overlapping collection approach is preferred because it has a greater probing depth range and larger fluorescence signal.

DESCRIPTION OF THE PREFERRED EMBODIMENT

Figure 9:
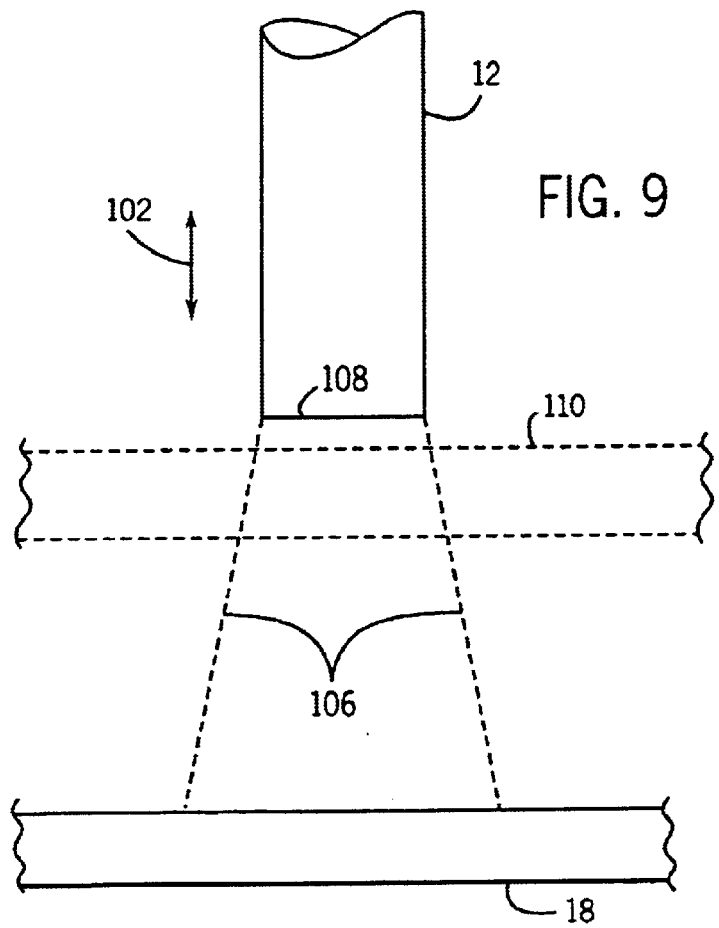
FIG. 9 is a schematic diagram of a portion of the instrument of FIG. 8.
Figure 8:
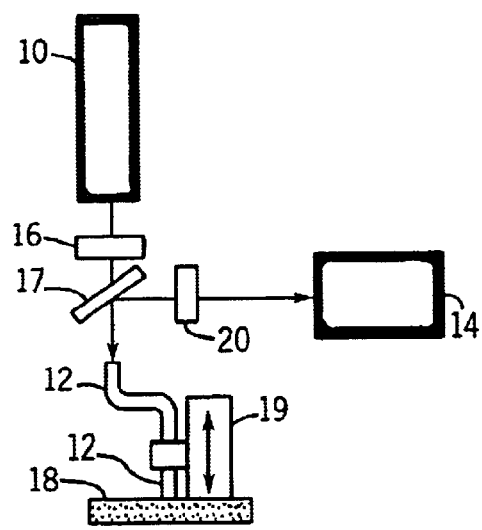
FIG. 8 is a pictorial representation of a fluorescence instrument, which employs one preferred embodiment of the invention.

FIG. 8 shows an overlapping collection embodiment of a fluorescence instrument which employs the present invention. The primary components are: a filtered white light source 10, an optical fiber imaging bundle 12 and a charged couple device (CCD) camera 14. The imaging bundle 12 consists of multiple optical fibers, each with the same diameter (100 $\mu$m). Monochromatic light is coupled via a beam expander 16 and dichroic filter 17 into the imaging bundle 12. Light incident on tissue 18 from each optical fiber generates fluorescence, which is collected by the same optic fiber 12, reflected at the dichroic filter 17 and coupled through a filter 20 to the CCD camera 14. The filter 20 may be a band pass filter for fluorescence measurements and a polarizer and neutral density filter to detect diffuse reflectance over the same dynamic range. The diameter of the illumination and collection area viewed by each optical fiber is varied from approximately 100 $\mu$m—1 mm in 100 $\mu$m diameter increments. This is achieved by translating the imaging bundle vertically from the sample surface in 100 μm increments using a motorized, high resolution translation stage indicated at 19. As the end of the imaging bundle is translated away from the tissue surface, the illumination/collection area for each fiber increases. This is illustrated in FIG. 9 where optical fiber 12 is translated as indicated by arrow 102 with respect to the surface of a tissue 18 under examination. The effective aperture of the fiber 12 increases as indicated by dotted lines 106 as a function of distance from its end surface 108. When the tissue surface is brought near the fiber end 108 as indicated by dashed lines 110, the aperture decreases in size to the area of the fiber end 108. The center-to-center distance between each optical fiber in the bundle 12 is fixed such that there is minimal overlap in the illumination and collection area of the neighboring optical fibers at the largest aperture diameter setting of 1 mm.

Figure 10:
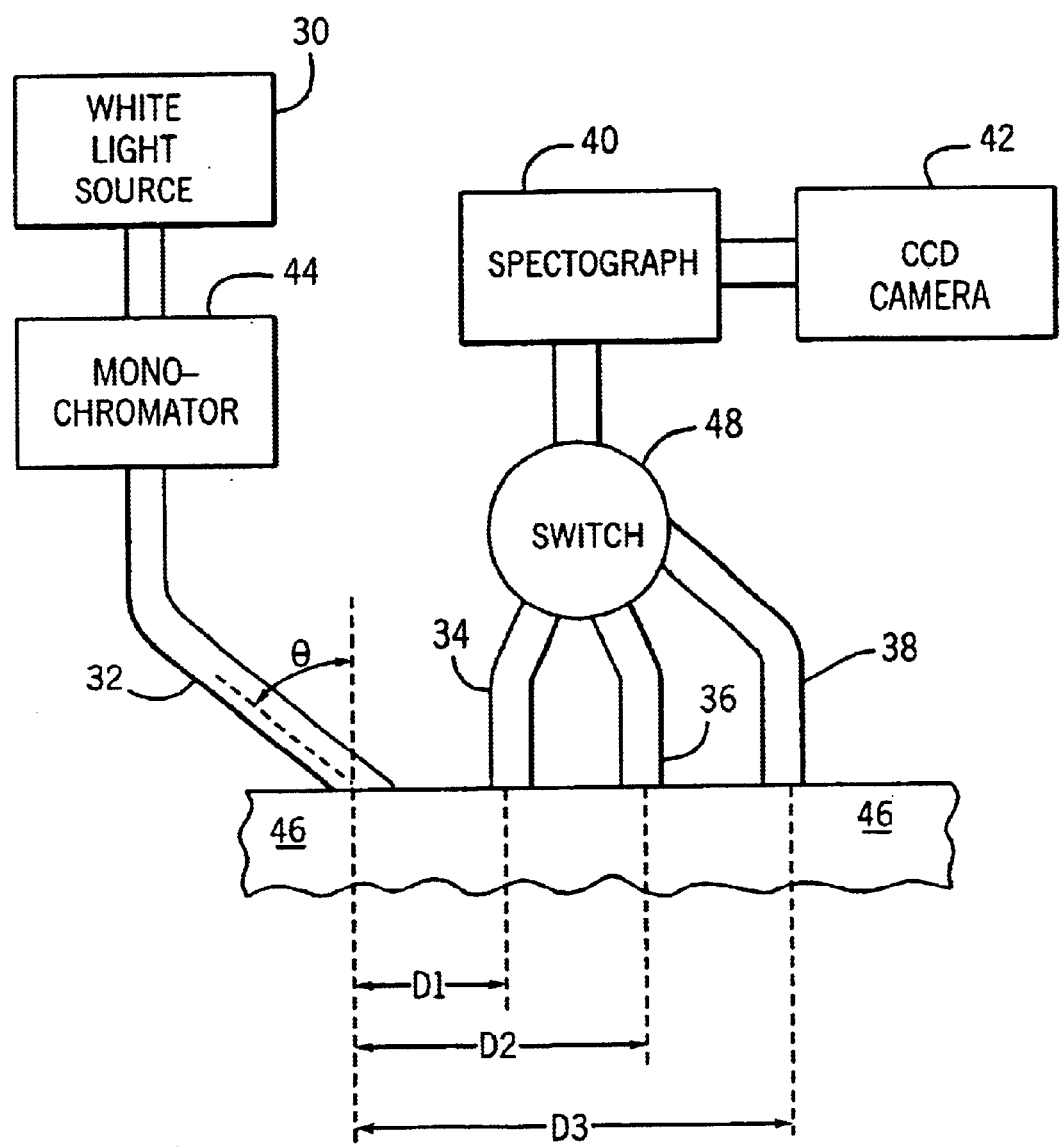
FIG. 10 is a pictorial representation of a second fluorescence instrument, which employs another preferred embodiment of the invention.

FIG. 10 shows another fluorescence instrument, which employs the present invention. This employs the non-overlapping collection technique described above. The primary components are: a filtered white light source 30, an illuminating optical fiber bundle 32, collection optical fiber bundles 34, 36 and 38 and a spectrograph 40 and a detector in the form of a charged couple device (CCD) camera 42. Light emanating from the white light source 30 contains a full spectrum, and a monochromator 44 allows only the light at a selected wavelength to pass through to the illumination bundle 32. The illumination bundle 32 consists of multiple optical fibers, each with the same diameter (200 μm). The illumination light is delivered to the surface of tissue 46 at an angle θ from perpendicular. In the preferred embodiment this angle θ is set to 45° since it has been found that this results in a peak fluorescence sensitivity at the depths necessary to measure SCC during its various stages.

The collection bundles 34, 36 and 38 are disposed in a line and are placed at different distances from the illumination bundle 32. The collection bundles 34, 36 and 38 are aligned in the direction of the tilted illuminating bundle 32 such that the tissue beneath them is illuminated. The light collected by the collection fibers 34, 36 and 38 is sent to an optical switch 48 which selects the light from one bundle at a time. Measurements of the fluorescence at each of the three collection distances $D_1$, $D_2$ and $D_3$ can thus be made in succession by operating the switch 48 and capturing the light. The light collected by the series of collection fibers 34, 36 and 38 is equivalent to light collected at variable aperture sizes.

Figure 11:
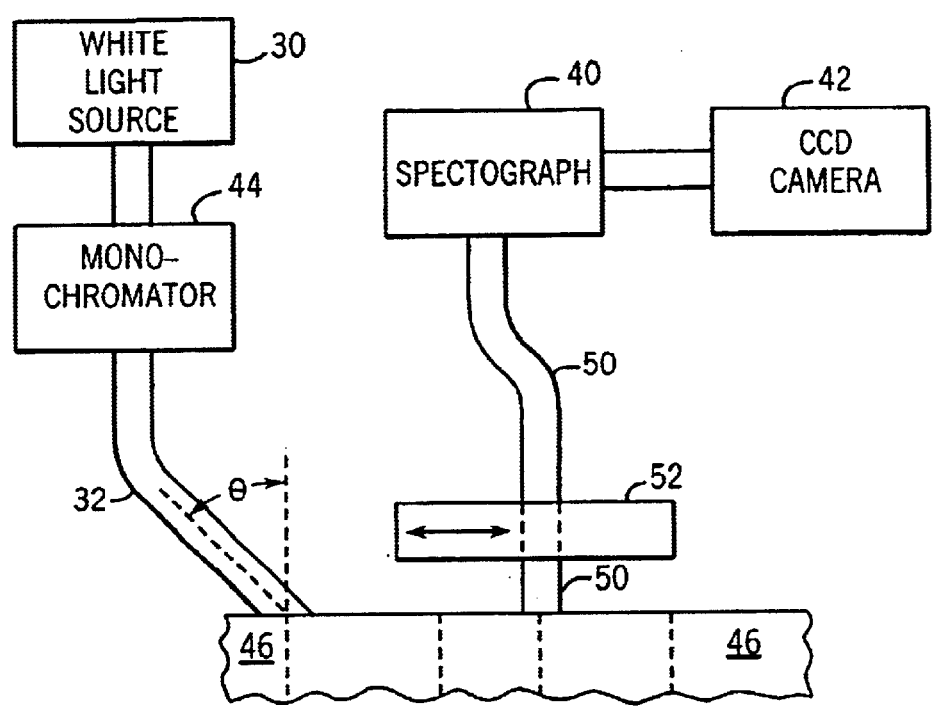
FIG. 11 is a pictorial representation of a third fluorescence instrument which employs the present invention.

Another embodiment of a fluorescence instrument which employs the non-overlapping illumination/collection technique is shown in FIG. 11. This instrument is similar to that described above and shown in FIG. 10 except a single optical fiber collection bundle 50 is employed. No optical switch is therefore needed, but the single collection bundle 50 is moved to different locations on the surface of tissue 46 by a motorized, high resolution translation stage indicated at 52. With this instrument a series of measurements are made with the collection bundle 50 positioned at a corresponding series of locations extending along a path directed away from the illumination bundle 32. These measurements are thus made at a series of different apertures.

While all three of the above-described fluorescence instruments can be used to acquire fluorescence data at varying depths below a tissue surface, it should be apparent that the embodiment shown in FIG. 10 is particularly applicable to endoscopic applications because there are no moving components. In the endoscopic application the illumination bundle 32 and the three collection fiber bundles 34, 36 and 38 are relatively long and extend to the distal end of the endoscope. They are molded into the fixed, relative positions shown in FIG. 10 at the distal end of the endoscope.

Figure 12:
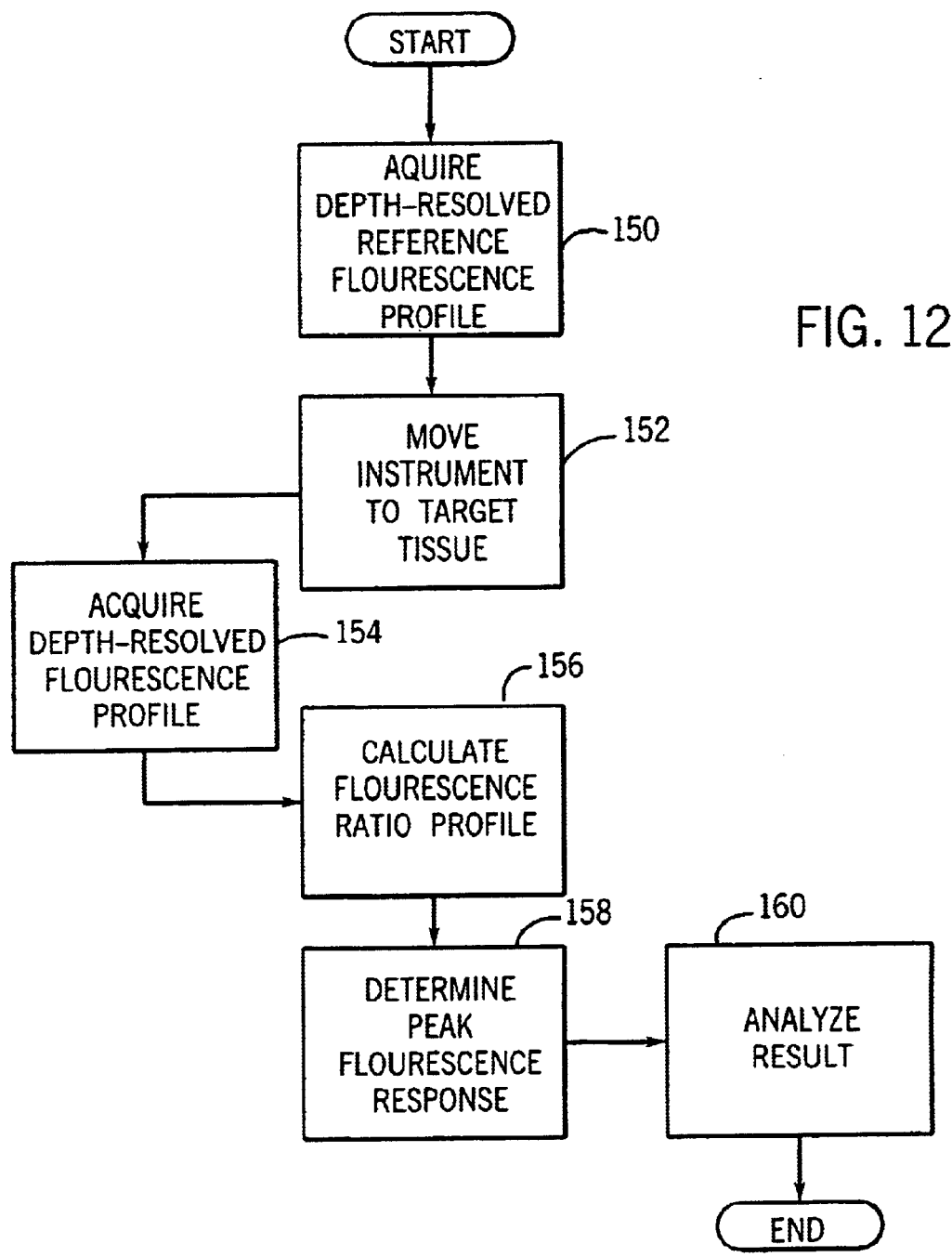
FIG. 12 is a flow chart indicating the steps used to practice the preferred method of using the fluorescence instrument.

Referring particularly to FIG. 12, regardless of which embodiment of the fluorescence instrument is used, a series of measurements are required to acquire sufficient data to assess fluorescence beneath a tissue surface. The first step as indicated at process block 150 is to position the instrument over the surface of "normal" tissue and acquire depth-resolved data. Light at a specific excitation wavelength is selected based on the particular fluorophores being examined and the normal tissue is illuminated at one aperture size. The fluorescence response is collected at this aperture and stored. Similar measurements are made at each of the prescribed aperture sizes and all the measured fluorescence responses are stored as a reference fluorescence profile. Preferably, these measurements are made a number of times and the results at each aperture setting averaged to provide a more robust reference profile.

As indicated at process block 152, the instrument is then moved to the surface of tissue which is the target of the examination. This may be done, for example, by manipulating an endoscope which carries the optical bundles of the instrument to the desired location. A fluorescence profile of the target tissue is then obtained as indicated at process block 154. This is a repeat of the fluorescence measurements made for the reference profile described above, but the data, of course, may be substantially different depending on the status of the target tissue. The acquired data is stored as a fluorescence profile.

As indicated at process block 156, the next step is to calculate a fluorescence ratio profile. This is performed by calculating the ratio of each aperture fluorescence measurement made at the target tissue and the corresponding aperture fluorescence reference measurement. A smooth curve is fit to the resulting ratio values at each aperture to form the fluorescence ratio profile. This profile of "normalized" fluorescence values is then examined at process block 158 to locate its peak value. As discussed above, the profile peak will be the minimum value in the profile when no exogenous fluorophore (GFP) is employed in the procedure (see FIG. 6a), and it will be the maximum value in the profile when an exogenous fluorophore is used (see FIG. 6b). The aperture value at this peak is an indicator of the depth of the fluorescent layer beneath the tissue surface. This "MFR" value may be used as indicated at process block 160 along with other information to analyze the target tissue.

The existence of the MFR size indicates the presence of the squamous cell carcinoma in the tissue. A smaller MFR size suggests a shallower position of the carcinoma while a greater MFR size suggests a deeper position of the carcinoma. The exact depth and thickness of the lesion/heterogeneity is difficult to extract from only the MFR size data as there are several other factors that can impact the relationship between them, such as the optical properties of the tissue. If all those other factors remain fixed, there exists a unique one-to-one mapping between the MFR diameter and the depth of the squamous cell carcinoma. In this case, a look-up table that maps the MFR diameter to the depth of the squamous cell carcinoma in the tissue can be constructed a priori and applied to finding the depth of the carcinoma. However, even in the absence of the information needed to map to a depth, this technique is an improved method for probing the fluorescence contrast from the squamous cell carcinoma at variable probing depths. The presence of a peak or valley in the fluorescence ratio profile is indicative of the presence of a fluorescent target.

What is claimed is:

1. A fluorescence instrument which comprises:

a light source for producing light;

illumination optical fiber for conveying the light to the surface of a subject to be examined and having an end disposed to direct light at a first location on said surface;

a collection optical fiber for collecting light emanating from the surface of the subject which is produced by fluorescence within the subject and beneath the surface, the optical fiber having an end disposed to receive light from a second location on said surface; and;

means for changing the effective aperture of the fluorescence instrument to enable fluorescence measurements of the subject to be made at different depths beneath the surface; and in which the means for changing includes means for changing the second location by moving the collection optical fiber to different positions relative to the illumination optical fiber.

2. A fluorescence instrument which comprises:

a light source for producing light;

illumination optical fiber for conveying the light to the surface of a subject to be examined and having an end disposed to direct light at a first location on said surface;

a collection optical fiber for collecting light emanating from the surface of the subject which is produced by fluorescence within the subject and beneath the surface, the optical fiber having an end disposed to receive light from a second location on said surface; and;

means for changing the effective aperture of the fluorescence instrument to enable fluorescence measurements of the subject to be made at different depths beneath the surface; and in which the collection means includes a plurality of said collection optical fibers, each having an end disposed to receive light from a corresponding different second location on said surface; and in which the means for changing includes means for separately connecting each of said collection optical fibers to a detector.

3. A fluorescence instrument which comprises:

a light source for producing light;

illumination optical fiber for conveying the light to the surface of a subject to be examined and having an end disposed to direct light at a first location on said surface;

a collection optical fiber for collecting light emanating from the surface of the subject which is produced by fluorescence within the subject and beneath the surface, the optical fiber having an end disposed to receive light from a second location on said surface; and;

means for changing the effective aperture of the fluorescence instrument to enable fluorescence measurements of the subject to be made at different depths beneath the surface; and in which the illumination optical fiber is oriented at an angle such that the light is directed at the surface of the subject at an angle θ from a direction perpendicular to the surface.

4. The fluorescence instrument as recited in claim 3 in which the subject is tissue and the angle θ is substantially 45°.

5. A fluorescence instrument which comprises:

a light source for producing light;

illumination optical fiber for conveying the light to the surface of a subject to be examined and having an end disposed to direct light at a first location on said surface;

a collection optical fiber for collecting light emanating from the surface of the subject which is produced by fluorescence within the subject and beneath the surface, the optical fiber having an end disposed to receive light from a second location on said surface; and;

means for changing the effective aperture of the fluorescence instrument to enable fluorescence measurements of the subject to be made at different deaths beneath the surface; and in which the means for changing the effective aperture includes means for moving the collection means relative to the illuminating means to change the distance between the illuminated surface of the subject and the surface of the subject from which light is collected.

6. A fluorescence instrument which comprises:

a light source for producing light;

illumination means for conveying the light to the surface of a subject to be examined;

collection means for collecting light emanating from the surface of the subject which is produced by fluorescence within the subject and beneath the surface;

a detector for measuring the collected light;

means for changing the effective aperture of the fluorescence instrument to enable a series of fluorescence measurements of the subject to be made at different depths beneath the surface; and in which the illuminating means and the collection means includes an optical fiber having an end positioned to direct light onto the surface of the subject and receive light emanating from the same surface; and the means for changing the effective aperture of the fluorescence instrument includes means for moving the end of the optical fiber to locations at different distances from the surface of the subject.

7. A method for probing beneath the surface of a target media at a selected location for a fluorescence layer, the steps comprising:

a) acquiring a depth-resolved reference fluorescence profile using a fluorescence instrument to probe at a series of different depths beneath the surface of the target media at a location of known characteristics;

b) acquiring a depth-resolved fluorescence profile using the fluorescence instrument to probe at the series of depths beneath the surface of the target media at the selected location;

c) calculate a fluorescence ratio profile using the reference fluorescence profile and the fluorescence profile; and d) examining the fluorescence ratio profile to detect the presence of the fluorescence layer.

8. The method as recited in claim 7 in which step d) includes determining the peak fluorescence response in the fluorescence ratio profile.

9. The method as recited in claim 8 which includes producing an indication of the depth of the fluorescence layer using information related to the peak fluorescence response.

10. The method as recited in claim 9 in which the target media is tissue and the fluorescence layer is squamous cell carcinoma in the tissue.

11. The method as recited in claim 7 in which step c) includes calculating the ratio of values at different depths in the reference fluorescence profile to values at corresponding depths in the fluorescence profile.

* * * * *